United States Patent
Hu

(10) Patent No.: US 11,845,714 B2
(45) Date of Patent: *Dec. 19, 2023

(54) PROCESS FOR PRODUCING TAURINE

(71) Applicant: Vitaworks IP, LLC, North Brunswick, NJ (US)

(72) Inventor: Songzhou Hu, Princeton, NJ (US)

(73) Assignee: Vitaworks IP, LLC, North Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,837

(22) Filed: Feb. 16, 2023

(65) Prior Publication Data

US 2023/0192602 A1 Jun. 22, 2023

Related U.S. Application Data

(63) Continuation of application No. 17/176,326, filed on Feb. 16, 2021, which is a continuation-in-part of application No. 16/030,605, filed on Jul. 9, 2018, now Pat. No. 10,961,183, which is a continuation of application No. 15/870,844, filed on Jan. 12, 2018, now Pat. No. 10,040,755, which is a continuation of
(Continued)

(51) Int. Cl.
| | |
|---|---|
| C07C 303/32 | (2006.01) |
| C07C 303/02 | (2006.01) |
| C07C 303/22 | (2006.01) |
| C07C 309/14 | (2006.01) |
| C07C 303/44 | (2006.01) |
| B01J 23/04 | (2006.01) |

(52) U.S. Cl.
CPC ......... *C07C 303/32* (2013.01); *C07C 303/02* (2013.01); *C07C 303/22* (2013.01); *C07C 303/44* (2013.01); *C07C 309/14* (2013.01); *B01J 23/04* (2013.01)

(58) Field of Classification Search
None
See application file for complete search history.

(56) References Cited

U.S. PATENT DOCUMENTS

| | | | |
|---|---|---|---|
| 1,926,691 A | 9/1933 | Swallen et al. | |
| 1,932,907 A | 10/1933 | Schmidt | |

(Continued)

FOREIGN PATENT DOCUMENTS

| | | |
|---|---|---|
| CH | 192027 A | 7/1937 |
| CN | 101260070 A | 9/2008 |

(Continued)

OTHER PUBLICATIONS

Wu et al., Optimization on Ammonolysis in Manufacturing Method of Taurine. 19:1 Journal of Hubei Polytechnic University 23-26; 2004 (Year: 2004).*

(Continued)

*Primary Examiner* — Karl J Puttlitz
(74) *Attorney, Agent, or Firm* — MYERS WOLIN, LLC

(57) ABSTRACT

There is disclosed a process for producing taurine in a molar yield of at least 80% from alkali isethionate, alkali ditaurinate, or alkali tritaurinate by adding excess ammonia and at least of equal molar amount of an alkali hydroxide to a solution comprised of alkali ditaurinate, alkali tritaurinate, or their mixture and subjecting the solution to an ammonolysis to yield a solution comprised of alkali taurinate.

19 Claims, 2 Drawing Sheets

Related U.S. Application Data application No. PCT/US2017/018527, filed on Feb. 17, 2017, which is a continuation of application No. 15/228,539, filed on Aug. 4, 2016, now Pat. No. 9,573,890, which is a continuation-in-part of application No. 14/120,651, filed on Jun. 12, 2014, now Pat. No. 9,428,451, which is a continuation-in-part of application No. 14/120,046, filed on Apr. 18, 2014, now Pat. No. 9,428,450.

(56) References Cited

U.S. PATENT DOCUMENTS

| | | | |
|---|---|---|---|
| 1,999,614 | A | 4/1935 | Schmidt et al. |
| 2,068,132 | A | 1/1937 | Herold et al. |
| 2,109,401 | A | 2/1938 | Schmidt |
| 2,192,523 | A | 3/1940 | Olin et al. |
| 2,658,072 | A | 11/1953 | Kosmin et al. |
| 2,693,488 | A | 11/1954 | Sexton |
| 2,820,818 | A | 1/1958 | Britton |
| 2,830,082 | A | 4/1958 | Sexton et al. |
| 2,880,219 | A | 3/1959 | Burnette et al. |
| 3,013,035 | A | 12/1961 | Huber et al. |
| 3,084,187 | A | 4/1963 | Gaetner, V et al. |
| 3,196,173 | A | 7/1965 | Willmund et al. |
| 3,882,181 | A | 5/1975 | Forster et al. |
| 3,894,064 | A | 7/1975 | Boehmke |
| 4,233,229 | A | 11/1980 | Chakrabarti |
| 4,288,368 | A | 9/1981 | Hangwitz |
| 4,352,759 | A | 10/1982 | Schwarte |
| 4,657,704 | A | 4/1987 | Yamamoto et al. |
| 5,434,276 | A | 7/1995 | Walele et al. |
| 6,562,874 | B1 | 5/2003 | Ilardi et al. |
| 8,609,890 | B1 | 12/2013 | Hu |
| 9,061,976 | B1 | 6/2015 | Hu |
| 9,108,907 | B1 | 8/2015 | Hu |
| 9,428,450 | B2 * | 8/2016 | Hu .................. C07C 303/32 |
| 9,428,451 | B2 | 8/2016 | Hu |
| 9,573,890 | B2 | 2/2017 | Hu |
| 9,593,076 | B2 | 3/2017 | Hu |
| 9,598,357 | B1 | 3/2017 | Hu |
| 9,598,360 | B2 | 3/2017 | Hu |
| 9,745,258 | B1 | 8/2017 | Hu |
| 9,815,778 | B1 | 11/2017 | Hu |
| 9,850,200 | B1 | 12/2017 | Hu |
| 9,926,265 | B1 | 3/2018 | Hu |
| 9,994,517 | B1 | 6/2018 | Hu |
| 10,040,755 | B2 | 8/2018 | Hu |
| 10,071,955 | B1 | 9/2018 | Yong et al. |
| 10,112,894 | B2 | 10/2018 | Hu |
| 10,131,621 | B2 | 11/2018 | Hu |
| 10,604,478 | B1 | 3/2020 | Sun et al. |
| 10,683,264 | B2 | 6/2020 | Hu |
| 10,793,517 | B2 | 10/2020 | Hu |
| 10,961,183 | B2 | 3/2021 | Hu |
| 11,254,639 | B1 | 2/2022 | Hu |
| 11,578,036 | B2 | 2/2023 | Hu |
| 11,623,914 | B2 | 4/2023 | Hu |
| 2014/0121405 | A1 | 5/2014 | Chen |
| 2015/0210633 | A1 | 7/2015 | Hu |
| 2015/0299113 | A1 | 10/2015 | Hu |
| 2016/0340300 | A1 | 11/2016 | Hu |
| 2016/0355470 | A1 | 12/2016 | Hu |
| 2018/0093946 | A1 | 4/2018 | Hu |
| 2018/0141899 | A1 | 5/2018 | Hu |
| 2018/0155278 | A1 | 6/2018 | Hu |
| 2018/0162806 | A1 | 6/2018 | Hu |
| 2019/0112260 | A1 | 4/2019 | Hu |
| 2019/0112261 | A1 | 4/2019 | Hu |
| 2019/0112262 | A1 | 4/2019 | Hu |
| 2019/0135739 | A1 | 5/2019 | Hu |

FOREIGN PATENT DOCUMENTS

| | | | |
|---|---|---|---|
| CN | 101486669 | A | 7/2009 |
| CN | 101508657 | A | 8/2009 |
| CN | 101508658 | A | 8/2009 |
| CN | 101508659 | A | 8/2009 |
| CN | 101717353 | A | 6/2010 |
| CN | 103382170 | A | 11/2013 |
| CN | 104003911 | A | 8/2014 |
| CN | 104016888 | A | 9/2014 |
| CN | 104513181 | A | 4/2015 |
| CN | 104628609 | A | 5/2015 |
| CN | 104803890 | A | 7/2015 |
| CN | 104945289 | A | 9/2015 |
| CN | 105209431 | A | 12/2015 |
| CN | 105693559 | A | 6/2016 |
| CN | 105732440 | A | 7/2016 |
| CN | 106008280 | A | 10/2016 |
| CN | 107056659 | A | 8/2017 |
| CN | 110551045 | A | 12/2019 |
| CN | 110590614 | A | 12/2019 |
| CN | 210215203 | U | 3/2020 |
| CN | 112010783 | A | 12/2020 |
| CN | 112010784 | A | 12/2020 |
| DE | 572 204 | | 3/1933 |
| DE | 1 122 540 | B | 1/1962 |
| DE | 1 157 234 | | 11/1963 |
| DE | 1 157 234 | B | 11/1963 |
| DE | 84394 | A | 9/1970 |
| DE | 219023 | A3 | 2/1985 |
| EP | 0 425 131 | A1 | 5/1991 |
| GB | 406788 | | 3/1934 |
| IN | 104945289 | A | 9/2015 |
| JP | 863-243066 | A | 10/1988 |
| JP | H04-352760 | A | 12/1992 |
| JP | 2937797 | B2 | 8/1999 |
| WO | 01/77071 | * | 10/2001 |
| WO | 0177071 | A1 | 10/2001 |
| WO | 2015/158157 | A1 | 10/2015 |
| WO | 2020/238942 | A1 | 12/2020 |
| WO | 2021/120957 | A1 | 6/2021 |
| WO | 2021/128917 | A1 | 7/2021 |
| WO | 2021/248077 | A1 | 9/2021 |
| WO | 2021/258005 | A1 | 12/2021 |

OTHER PUBLICATIONS

Translation of Wu from Final Written Decision of IPR2018-01766, Reexamination of U.S. Pat. No. 9,428,450 issued from U.S. Appl. No. 14/120,046 (Year: 2004).*

Liu; Fuming, Process Design of Taurine Ammonolysis, 5:8 China Chemical Trade 120 (2013) (Year: 2013).*

Translation of Liu from Final Written Decision of IPR2018-01766, Reexamination of U.S. Pat. No. 9,428,450 issued from U.S. Appl. No. 14/120,046 (Year: 2013).*

Final Written Decision of IPR2018-01766, Reexamination of U.S. Pat. No. 9,428,450 issued from U.S. Appl. No. 14/120,046 (Year: 2020).*

Translation of WO 01/77071 from Final Written Decision of IPR2018-01766, Reexamination of U.S. Pat. No. 9,428,450 issued from U.S. Appl. No. 14/120,046 (Year: 2001).*

Kennedy, "QYP Defendants Invalidity Contentions for U.S. Pat. Nos. 9,745,258; 9,815,778; 9,926,265", dated Aug. 12, 2021, 72 pages.

Kennedy, "QYP Defendants Invalidity Contentions for U. S. Pat. Nos. 10,040,755; 10,961, 183", dated Jan. 7, 2022, 123 pages.

QYP Defendants Invalidity Contentions: Exhibits A-E, dated Jan. 7, 2022, 243 pages.

Goswami et al., "Vitaworks IP, LLC et al. Response to Invalidity Contentions for U.S. Pat. Nos. 9,745,258; 9,815,778; 9,926,265", dated Oct. 11, 2021, 122 pages.

Goswami et al., "Vitaworks' Supplemental Response to Invalidity Contentions for U.S Pat. Nos. 10,040,755; 10,961, 183", dated Feb. 7, 2022, 215 pages.

"Vitaworks' et al. Response—Validity Charts: Exhibits I-V", dated Feb. 7, 2022, 234 pages.

Wilson et al., "Defendants' Invalidity Contentions" for U.S. Pat. Nos. Re. 48,238 (the "238 patent"); Re. 48,333 (the "333 patent")Re. 48,354 (the "'354 patent"); Re. 48,369 (the "'369 patent"); and Re.

(56) References Cited

OTHER PUBLICATIONS 48,392 (the "'392 patent"), as well as of U.S. Pat. Nos. 9,598,357 (the "'357 patent"), 10,040,755 (the "'755 patent"), and 10,961,183 (the "'183 patent"), dated Mar. 2, 2023, 275 pages.
Dellinger et al., "Joint Claim Construction Brief", dated Apr. 29, 2022, 97 pages.
Dellinger et al., "Appendix in Support of Joint Claim Construction Brief", dated Apr. 29, 2022, 201 pages.
Williams, "Memorandum Opinion", dated Jan. 23, 2023, 20 pages, Wilmington, DE.
Patent Owner's Preliminary Response for Inter Partes Review of U.S. Pat. No. 9,428,450 IPR2018-01766, dated Jan. 11, 2019, 50 pages.
Patent Owner's Preliminary Response for Inter Partes Review of U.S. Pat. No. 9,428,451 IPR2018-01767, dated Jan. 14, 2019, 62 pages.
Patent Owner's Preliminary Response for Inter Partes Review of U.S. Pat. No. 9,573,890 IPR2018-01768, dated Jan. 16, 2019, 54 pages.
Robert E. Maleczka's Declaration in Support of Patent Owner's Preliminary Response for Inter Partes Review of U.S. Pat. No. 9,428,450 IPR2018-01766, dated Jan. 11, 2019, 60 pages.
Robert E. Maleczka's Declaration in Support of Patent Owner's Preliminary Response for Inter Partes Review of U.S. Pat. No. 9,428,451 IPR2018-01767, dated Jan. 14, 2019, 75 pages.
Robert E. Maleczka's Declaration in Support of Patent Owner's Preliminary Response for Inter Partes Review of U.S. Pat. No. 9,573,890 IPR2018-01768, dated Jan. 16, 2019, 67 pages.
Patent Owner's Response for Inter Partes Review of U.S. Pat. No. 9,428,450, IPR2018-01766, dated Jul. 12, 2019, 66 pages.
Robert E. Maleczka's 2nd Declaration in Support of Patent Owner's Response for Inter Partes Review of U.S. Pat. No. 9,428,450, IPR2018-01766, dated Jul. 12, 2019, 81 pages, Vitaworks Exhibit 2007.
Curriculum Vitae (CV) of Robert E. Maleczka, as of Jul. 12, 2019, 39 pages, Vitaworks Exhibit 2008.
Decision re Institution of Inter Partes Review issued for Case IPR2018-01766 for corresponding U.S. Pat. No. 9,428,450, Dated Apr. 9, 2019, 45 pages.
Decision re Institution of Inter Partes Review issued for Case IPR2018-01767 for corresponding U.S. Pat. No. 9,428,451, dated Apr. 10, 2019, 25 pages.
Decision re Institution of Inter Partes Review issued for Case IPR2018-01768 for corresponding U.S. Pat. No. 9,573,890, dated Apr. 10, 2019, 23 pages.
Objective Indicia filed with Response dated Jul. 25, 2019, 11 pages. Results for experiments conducted between May 14, 2019 and Jun. 30, 2019, Vitaworks Exhibits 2009-2065.
Objective Indicia Exhibit A: Excerpt from "Bulletin of Ministry of Environment Protection of China", Jan. 27, 2015, with English summary, and excerpt from "Environment Impact Assessment Report of 25,000/Year Taurine Plant of Hubei Grand Life Science and Technology Co. Ltd.", dated Jul. 24, 2017, with English summary.
Objective Indicia Exhibit B: "Production Flowchart of Taurine in Environmental Impact Assessment Report of Jiangying Huachang Food Additive Company", 2005, with English translation of flowchart.
Objective Indicia Exhibit C: "Production Flowchart of Taurine in Amended Environmental Impact Assessment Report of Jiangying Huachang Food Additive Company", 2017, with English translation of flowchart.
Objective Indicia Exhibit D: Selected Pages from Qiangjiang Yongan Pharmaceutical Co. Annual Reports 2012-2015, with partial English translations.
Objective Indicia Exhibit G: "Study of the Ammonolysis Reaction for Taurine" Liu 2015; Liu Fuming & Xie Liming, Shandong Chemical Industry, May 2015, vol. 44, No. 5, pp. 27-28, 30, with English translations.
Objective Indicia Exhibit H: Liu 2013, Liu Fuming, China Chemical Trade Monthly Journal, Aug. 2013, vol. 5, Issue. 8, HGL Exhibit 1019.

Objective Indicia Exhibit I: Wu 2004, Wu Jiang & Guan Zailin J., Journal of Hubei Polytechnic University, Feb. 2004, vol. 19, No. 1, pp. 23-26, HGL Exhibit 1016.
Notice of Allowance issued by the United States Patent and Trademark Office for corresponding U.S. Appl. No. 14/120,046, dated onically delivered on May 24, 2016.
Notice of Allowance issued by the United States Patent and Trademark Office for corresponding U.S. Appl. No. 14/120,046, dated Jul. 14, 2016.
Notice of Allowance issued by the United States Patent and Trademark Office for corresponding U.S. Appl. No. 15/238,621, dated Oct. 5, 2016.
Non-Final Office Action issued by the United States Patent and Trademark Office for corresponding U.S. Appl. No. 15/228,539, dated Oct. 17, 2016.
Final Office Action issued by the United States Patent and Trademark Office for corresponding U.S. Appl. No. 14/120,046, dated Dec. 8, 2015.
Notice of Allowance issued by the United States Patent and Trademark Office for corresponding U.S. Appl. No. 15/228,539, dated Dec. 23, 2016.
Notice of Allowance issued by the United States Patent and Trademark Office for corresponding U.S. Appl. No. 15/238,621, dated Jan. 4, 2017.
Notice of Allowance issued by the United States Patent and Trademark Office for corresponding U.S. Appl. No. 15/228,568, dated Jan. 17, 2017.
Notice of Allowance issued by the United States Patent and Trademark Office for corresponding U.S. Appl. No. 14/120,651, dated Aug. 2, 2016.
Non-Final Office Action of Reissue U.S. Appl. No. 16/863,384 for U.S. Pat. No. 9,428,451 B2, dated Sep. 22, 2020, 34 pages.
Non-Final Office Action of Reissue U.S. Appl. No. 16/842,389 for U.S. Pat. No. 9,573,890 B2, dated Sep. 22, 2020, 31 pages.
Non-Final Office Action of Reissue U.S. Appl. No. 16/853,395 for U.S. Pat. No. 9,428,450 B2, dated Sep. 9, 2020, 26 pages.
Notice of Allowance of Reissue U.S. Appl. No. 16/842,389 for U.S. Pat. No. 9,573,890 B2, dated Oct. 21, 2020, 9 pages.
Notice of Allowance of Reissue U.S. Appl. No. 16/863,384 for U.S. Pat. No. 9,428,451 B2, dated Oct. 29, 2020, 8 pages.
Notice of Allowance of Reissue U.S. Appl. No. 16/854,395 for U.S. Pat. No. 9,428,450 B2, dated Oct. 29, 2020, 8 pages.
Liu Fuming Process Design of the Ammonolysis Reaction of Taurine, China Chemical Trade, 2013, No. 8, pp. 120. (Original article is published in China in Chinese, a English translation by the Applicant is included).
Liu Fuming, Xie Liming Study on the Ammonolysis Reaction For Taurine, Shandong Chemical Industry, 2015, 44 (5), pp. 27-28,30 (Original article is published in Chinese. An English translation by the Applicant is included).
International Search Report for corresponding International Application No. PCT/CN2015/000232, dated Jul. 1, 2015.
Extended European Search Report and the European Search Opinion completed Apr. 5, 2017 for corresponding European Application No. 17157022.9.
USPTO Non-Final Office Action for corresponding U.S. Appl. No. 15/228,568 dated Oct. 5, 2016.
USPTO Non-Final Office Action for corresponding U.S. Appl. No. 14/120,651 dated Mar. 15, 2016.
International Search Report and Written Opinion for corresponding International Application No. PCT/US2017/018527, dated Jun. 8, 2017.
Japanese Notice of Reasons for Rejection, dated Jun. 13, 2017 with English machine translation, for corresponding Japan application No. 2017-033759.
USPTO Non-Final Office Action for corresponding U.S. Appl. No. 15/228,539 dated Oct. 17, 2016.
USPTO Non-Final Office Action for corresponding U.S. Appl. No. 15/120,046 dated Aug. 26, 2015.
Canadian First Office Action, dated Nov. 2, 2017 for corresponding Canada Application No. 2,946,181.

(56) References Cited

OTHER PUBLICATIONS

Office Action issued by the Canadian Intellectual Property Office for corresponding Canadian Patent Application No. 2,946, 181, dated Mar. 26, 2018.
Notification of Reasons for Rejection issued by the Japan Patent Office for corresponding Japanese Patent Application No. 2017-505693, dated Mar. 27, 2018, with an English translation.
Extended European Search Report issued by the European Patent Office for corresponding European Patent Application No. EP18154790. 2, dated Jun. 25, 2018.
Goswami et al., Vitaworks' Response to Defendants' Invalidity Contentions for U.S. Pat. Nos. Re. 48,238 (the "238 patent"); Re. 48,333 (the "'333 patent")Re. 48,354 (the "354 patent"); Re. 48,369 (the "'369 patent"); and Re. 48,392 (the "392 patent"), as well as of U.S. Patent Nos. 9,598,357 (the "357 patent"), 10,040,755 (the "755 patent"), and 10,961,183 (the "183 patent"), Secondary Considerations, dated Jan. 12, 2023, 49 pages.
Notice of Allowance issued by the United States Patent and Trademark Office for U.S. Appl. No. 16/843,272, dated Aug. 25, 2020.
Notice of Allowance issued by the United States Patent and Trademark Office for U.S. Appl. No. 16/854,406, dated Aug. 26, 2020.
Declaration Under 37 C.F.R. § 1.132 By Dr. Songzhou Hu, Dated Apr. 8, 2020, 25 pages.
Goswami et al., Vitaworks' Response to Invalidity Contentions for U.S. Pat. Nos. Re. 48,238 (the "'238 patent"); Re. 48,333 (the "333 patent")Re. 48,354 (the "354 patent"); Re. 48,369 (the "369 patent"); and Re. 48,392 (the "392 patent"), as well as of U.S. Pat. Nos. 9,598,357 (the "357 patent"), 10,040,755 (the "755 patent"), and 10,961, 183 (the "'183 patent"), dated Apr. 6, 2023, 307 pages.
Goswami et al., Vitaworks' Response to Defendants' Invalidity Contentions for U.S. Pat. Nos. Re. 48,238 (the "238 patent"); Re. 48,333 (the "'333 patent")Re. 48,354 (the "354 patent"); Re. 48,369 (the "'369 patent"); and Re. 48,392 (the "392 patent"), as well as of U.S. Pat. Nos. 9,598,357 (the "357 patent"), 10,040,755 (the "755 patent"), and 10,961,183 (the "183 patent"), Secondary Considerations, dated Jan. 12, 2023, 49 pages.
Declaration Under 37 C.F.R. § 1.132 By Dr. Songzhou Hu, Submitted in U.S. Appl. No. 16/843,272 dated Apr. 3, 2020, 25 pages.
*Yeda Research and Development Co., Ltd., v. Abbott Gmbh & Co. Kg*, 15-1662 (Fed. Cir. 2016)Opinion, Sep. 20, 2016, 8 pages.
Final Office Action issued by the United States Patent and Trademark Office for U.S. Appl. No. 16/030,605, dated Nov. 30, 2020.
Marvel et al., "A Synthesis of Taurine", Contribution from the Chemical Laboratory of the University of Illinois, Jul. 1927, pp. 1833-1837, vol. 49., Illinois, USA.
A. C. Stevenson, "Ammonolysis", Industrial and Engineering Chemistry, Sep. 1948, pp. 1584-1589, vol. 40, No. 9.
G. H. Goleman, "Ammonolysis", Industrial and Engineering Chemistry, Sep. 1953, pp. 1915-1920, vol. 45, No. 9.
Tsang et al., An Activated Sulfonylating Agent That Undergoes General Base-Catalyzed Hydrolysis by Amines in Preference to Aminolysis, J. Org. Chem., 2008, pp. 4504-4512, vol. 73, No. 12.
H. F. Rase, "Handbook of Commercial Catalysts—Heterogeneous Catalysts", CRC Press, 2000, pp. 37-41.
Soroka et al., "Comments on a New Simple Route to N-Substituted 2-Aminoethylphosphonic Acid. A Reinvestigation", Synth. Commun., 2003, pp. 3781-3788, vol. 33, No. 21.
Bulychev et al., "Commercial Synthesis of 2-Aminoethanesulfonci Acid (Taurine)", Pharmceutical Chem. J., Mar. 2013, pp. 740-742, vol. 46, No. 12.
Hu et al., "Efficient Synthesis of Taurine and Structurally Diverse Substituted Taurine from Aziridines", J. Org. Chem., 2007, pp. 4543-4546, vol. 72.
Jencks et al., "General Base Catalysis of the Aminolysis of Phenyl Acetate", Contribution from the Graduate Department of Biochemistry, Brandeis University, Feb. 1960, pp. 675-681.
Kakemi et al., "General Base Catalyzed Hydrolysis of Furylmethylketone Isonicotinoylhydrazone", Chem. Pharm. Bull., 1970, pp. 834-838, vol. 18, No. 4.

A.A. Goldberg, "Taurine", Research Laboratories, Ward Blenkinsop Ltd., Bradford-On-Avon, 1943, pp. 4-5.
F. Cortese, "On the Synthesis of Taurine", Feb. 1936, pp. 191-192, vol. 58.
Campanema et al., "Oxidative Ammonolysis of Technical Lignins. Part 4. Effects of the Ammonium Hydroxide Concentration and pH", J. Wood Chemistry and Technology, 2006, pp. 95-109, vol. 26.
Widiyarti et al., "Preparation of 2-Aminoethylsulfonic Acid", Makara, Sains, Apr. 2009, pp. 55-58, vol. 13, No. 1, Indonesia.
Groggins et al., "Recent Progress in Amination by Ammonolysis", Industrial and Engineering Chemistry, Dec. 1937, pp. 1353-1361, vol. 29, No. 12.
Bayarmaa et al., "Synthesis and characterization of Taurine", Mongolian J. Chem., 2013, pp. 57-60, vol. 14, No. 40, Mongolia.
Schick et al., "Synthesis of Taurine and N-Methyltaurine", Industrial and Engineering Chemistry, 1942, pp. 906-909, vol. 39, No. 7.
Lauer et al., "The Addition of Sodium Bisulfite to Alkylene Oxides", Contribution from the School of Chemistry of the University of Minnesota, Oct. 1936, pp. 1873-1874, vol. 58.
Chen et al., The Process of Preparation of Taurine from Ethyleneimine, Zhejiang Chemical Industry, 2011, vol. 42, No. 05, pp. 18-20, China.
John Wiley & Sons, "Ammonium Compounds", Kirk-Othmer Encyclopedia of Chemical Technology, 1963, pp. 711-762, vol. 2.
S. A. Lawrence, "Substitution on the Amine Nitrogen", Science of Synthesis, 40.1, 2009, pp. 501-577.
Görbitz et al., "Taurine", Acta Crystallographica Section C., 2000, C56, e23-e24.
McMaster et al., "The Neutral Ammonium Salts of Some Substituted Benzoic Acids", 1915, pp. 2181-2188.
Kobe et al., "The Preparation of Ammonium Hydroxide for Laboratory Use", Journal of Chemical Education, vol. 18, No. 1, Jan. 1941, pp. 29-30.
USPTO Non-Final Office Action for corresponding U.S. Appl. No. 15/870,844 dated May 10, 2018.
JSPTO Notice of Allowance for corresponding U.S. Appl. No. 15/870,844 dated Jun. 15, 2018.
*Hubei Grans Life Science and Technology Co., Ltd v. Vitaworks IP, LLC*, Case No. IPR2018-01766, Petition for Inter Parte Review of U.S. Pat. No. 9,428,450 Under 37 C.F.R. § 42.100, Sep. 28, 2018, pp. 80 Alexandria, Virginia.
*Jubei Grans Life Science and Technology Co., Ltd v. Vitaworks IP, LLC*, Case No. IPR2018-01767, Petition for Inter Parte Review of U.S. Pat. No. 9,428,451 Under 37 C.F.R. § 42.100, Sep. 28, 2018, pp. 88, Alexandria, Virginia.
*Hubei Grans Life Science and Technology Co., Ltd v. Vitaworks IP, LLC*, Case No. IPR2018-01768 Petition for Inter Parte Review of U.S. Pat. No. 9,573,890 Under 37 C.F.R. § 42.100, Sep. 28, 2018, pp. 82, Alexandria, Virginia,.
Declaration of Mark A. Lipton in Support of Petition for Inter Partes Review of U.S. Pat. No. 9,428,450 Under 37 C.F.R. § 42.100, Sep. 28, 2018, pp. 65.
Declaration of Mark A. Lipton in Support of Petition for Inter Partes Review of U.S. Pat. No. 9,428,451 Under 37 C.F.R. § 42.100, Sep. 28, 2018, pp. 69.
Declaration of Mark A. Lipton in Support of Petition for Inter Partes Review of U.S. Pat. No. 9,573,890 Under 37 C.F.R. § 42.100, Sep. 28, 2018, pp. 66.
Bondavera et al., Pharmaceutical Chemistry Journal, Synthesis of Taurine, Mar. 2008, pp. 142-144, vol. 42, No. 3, Springer Science+ Business Media, Inc, Secaucus, New Jersey.
Liu Fuming, China Chemical Trade, Process Design of Taurine, Year 2013, p. 120, vol. 5, No. 6, China National Chemical Center, Beijing City, China http://chemmedia.com.cn/GotoBin/Select.DLL.
Journal of Hubei Institute of Technology, Opimization on Ammonolysis in Manufacturing Method of Taurine, Year 2004, pp. 23-26, vol. 19, No. 1, Sum No. 66, Editorial Department of Journal of Hubei Polytechnic University, Wuhan, China.
Petitioner's Reply to Patent Owner's Response for Inter Partes Review of U. S. Pat. No. 9,428,450, IPR2018-01766, dated Oct. 7, 2019, 38 pages.
Patent Owner's Surreply for Inter Partes Review of U. S. Pat. No. 9,428,450, IPR2018-01766, dated Nov. 15, 2019, 33 pages.

(56) References Cited

OTHER PUBLICATIONS

Final Written Decision for Inter Partes Review of U. S. Pat. No. 9,428,450, IPR2018-01766, dated Apr. 2, 2020, 65 pages.
Declaration of Mark A. Lipton in Support of Peitioner's Reply To Patent Owner's Response dated Oct. 7, 2019, 33 pages.
Declaration of Joe P. Foley, Ph.D. in Support of Peitioner's Reply To Patent Owner's Response, dated Oct. 7, 2019, 34 pages.
Maleczka, R. E., Supplemental Declaration of Robert E. Maleczka, Jr., Ph.D., IPR2018-01766, Exhibit 2006, 8 pages.
Protest Under 37 C.F.R. 1.291(a) against Reissue U.S. Appl. No. 16/843,272, Dated Jul. 17, 2020, 14 pages.
Protest Under 37 C.F.R. 1.291(a) against Reissue U.S. Appl. No. 16/854,395, Dated Jul. 17, 2020, 14 pages.
Protest Under 37 C.F.R. 1.291(a) against Reissue U.S. Appl. No. 16/854,406, Dated Jul. 17, 2020, 14 pages.
Protest Under 37 C.F.R. 1.291(a) against Reissue U.S. Appl. No. 16/842,389, Dated Jul. 28, 2020, 20 pages.
Protest Under 37 C.F.R. 1.291(a) against Reissue U.S. Appl. No. 16/863,384, Dated Aug. 3, 2020, 26 pages.
Notice of Allowance, Reissue U.S. Appl. No. 16/843,272, dated Aug. 25, 2020, 12 pages.
Notice of Allowance, Reissue U.S. Appl. No. 16/854,406, dated Aug. 26, 2020, 12 pages.
Non Final Office Action, U.S. Appl. No. 16/030,605, dated Aug. 9, 2018, 17 pages.
Final Office Action, U.S. Appl. No. 16/030,605, dated Jan. 30, 2019, 38 pages.
Non Final Office Action, U.S. Appl. No. 16/030,605, dated Oct. 28, 2019, 39 pages.
Final Office Action, U.S. Appl. No. 16/030,605, dated Jun. 29, 2020, 47 pages.
Non Final Office Action, U.S. Appl. No. 16/030,605, dated Jul. 28, 2020, 19 pages.
Final Office Action, U.S. Appl. No. 16/030,605, dated Nov. 30, 2020, 22 pages.

\* cited by examiner

PROCESS FOR PRODUCING TAURINE

CROSS REFERENCE TO RELATED APPLICATIONS

This is a continuation of U.S. application Ser. No. 17/176,326, filed on Feb. 16, 2021, which is a continuation-in-part of the U.S. application Ser. No. 16/030,605, filed on Jul. 9, 2018, now U.S. Pat. No. 10,961,183, which is a continuation of the U.S. application Ser. No. 15/870,844, filed on Jan. 12, 2018, now U.S. Pat. No. 10,040,755, which is a continuation of the national stage of PCT/US2017/018527, filed on Feb. 17, 2017, which is the U.S. application Ser. No. 15/228,539, filed on Aug. 4, 2016, now U.S. Pat. No. 9,573,890, reissued as U.S. RE48,369, which is a continuation-in-part of U.S. application Ser. No. 14/120,651, filed on Jun. 12, 2014, now U.S. Pat. No. 9,428,451, reissued as U.S. RE48,392, which is a continuation-in-part of U.S. application Ser. No. 14/120,046, filed on Apr. 18, 2014, now U.S. Pat. No. 9,428,450, reissued as U.S. RE48,238, U.S. RE48,333, and U.S. RE48,354, all of which are incorporated herein by reference.

TECHNICAL FIELD

The present invention relates to a cyclic process for the production of taurine from alkali isethionate and from alkali vinyl sulfonate in a high overall yield, i.e., greater than 90%, in particular, greater than 95%, by continuously converting the byproducts of the ammonolysis reaction, alkali ditaurinate and alkali tritaurinate, to alkali taurinate.

BACKGROUND OF THE INVENTION

Taurine can be referred to as 2-aminoethanesulfonic acid and is one of the amino sulfonic acids found in the tissues of many animals. Taurine is an extremely useful compound because it has such pharmacological effects as detoxification effect, fatigue-relieving effect and nourishing and tonifying effect. As a result, taurine finds wide applications as an essential ingredient for human and animal nutrition.

Taurine is currently produced in an amount of over 60,000 tons per year from ethylene oxide and monoethanolamine. At present time, most of the taurine is produced from ethylene oxide, following a three-step process: (1) the addition reaction of ethylene oxide with sodium bisulfite to yield sodium isethionate; (2) the ammonolysis of sodium isethionate to yield sodium taurinate; (3) the neutralization with an acid, i.e., hydrochloric acid and, preferably, sulfuric acid, to generate taurine and inorganic salts.

Although the ethylene oxide process is well established and widely practiced in commercial production, the overall yield is not very high, less than 80%. Moreover, the process generates a large amount of waste stream that is increasingly difficult to dispose of.

The first stage of the ethylene oxide process, the addition reaction of ethylene oxide with sodium bisulfite, is known to yield sodium isethionate in high yield, practically quantitative, as disclosed in U.S. Pat. No. 2,820,818 under specified conditions.

Therefore, the problems encountered in the production of taurine from the ethylene oxide process arise from the ammonolysis of sodium isethionate and from the separation of taurine from sodium sulfate.

U.S. Pat. No. 1,932,907 discloses that sodium taurinate is obtained in a yield of 80%, when sodium isethionate undergoes ammonolysis reaction in a molar ratio of 1:6.8 for 2 hrs at 240 to 250° C. U.S. Pat. No. 1,999,614 describes the use of catalysts, i.e., sodium sulfate, sodium sulfite, and sodium carbonate, in the ammonolysis reaction. A mixture of sodium taurinate and sodium ditaurinate is obtained in a yield as high as 97%. However, the percentage for sodium taurinate and sodium ditaurinate in the mixture is not specified.

DD 219 023 describes detailed results on the product distribution of the ammonolysis reaction of sodium isethionate. When sodium isethionate undergoes the ammonolysis reaction with 25% aqueous ammonia in a molar ratio of 1:9 at about 280° C. for 45 minutes in the presence of sodium sulfate and sodium hydroxide as catalyst, the reaction products comprise 71% of sodium taurinate and 29% of sodium di- and tri-taurinate.

WO 01/77071 is directed to a process for the preparation of ditaurine by heating an aqueous solution of sodium taurinate at a temperature of 210° C. in the presence of a reaction medium. A mixture of sodium taurinate and sodium ditaurinate is obtained.

From these prior arts, it is therefore concluded that the ammonolysis of sodium isethionate invariably yields a mixture of sodium taurinate, sodium ditaurinate, and sodium tritaurinate. The percentage yield of sodium taurinate has not been more than 80%.

In order to obtain taurine from sodium taurinate, U.S. Pat. No. 2,693,488 discloses a method of using ion exchange resins, first strongly acid ion exchange resin in hydrogen form, and then an anion exchange resin in basic form. This process is complicated and requires the use of large quantity of acid and base to regenerate the ion exchange resins in each production cycle.

On the other hand, CN101508657, CN101508658, CN101508659, and CN101486669 describe a method of using sulfuric acid to neutralize sodium taurinate to obtain a solution of taurine and sodium sulfate. Crude taurine is easily obtained by filtration from a crystalline suspension of taurine after cooling. However, the waste mother liquor still contains taurine, sodium sulfate, and other unspecified organic impurities. It is desirable to have available a process for further separation of these components to achieve an economical process and to reduce the amount of waste stream.

It is, therefore, an object of the present invention to disclose a cyclic process for the production of taurine from alkali isethionate and from alkali vinyl sulfonate in a high overall yield, i.e., greater than 90%, in particular, greater than 95%. According to the process in the present invention, sodium ditaurinate and sodium tritaurinate, byproducts from the ammonolysis of sodium isethionate or sodium vinyl sulfonate, are continuously converted to sodium taurinate in the ammonolysis stage.

It is another object of the present invention to disclose a process for the preparation of pure sodium ditaurinate and pure sodium tritaurinate, and their conversion to sodium taurinate. When sodium ditaurinate and sodium tritaurinate are reacted with aqueous ammonia under ammonolysis reaction conditions, a mixture of similar compositions of sodium taurinate, ditaurinate, and tritaurinate is formed in an equilibrium state. This novel finding renders the cyclic process possible.

It is a further object of the present invention to disclose a process for the complete separation of taurine and sodium sulfate from each other and from the byproducts, i.e., sodium ditaurinate and sodium tritaurinate. According to the process in the present invention, the residual taurine and sodium sulfate are separated from sodium ditaurinate and sodium tritaurinate by a process of co-crystallization of taurine and Glauber's salt at a temperature from 0 to 20° C. The crystalline mixture of taurine and sodium sulfate is then separated from each other, while the mother liquor, consisting of taurine, monosodium ditaurinate, and monosodium tritaurinate, is suitable for recycling to the ammonolysis step to prepare sodium taurinate.

DESCRIPTION OF THE INVENTION

Figure 1:
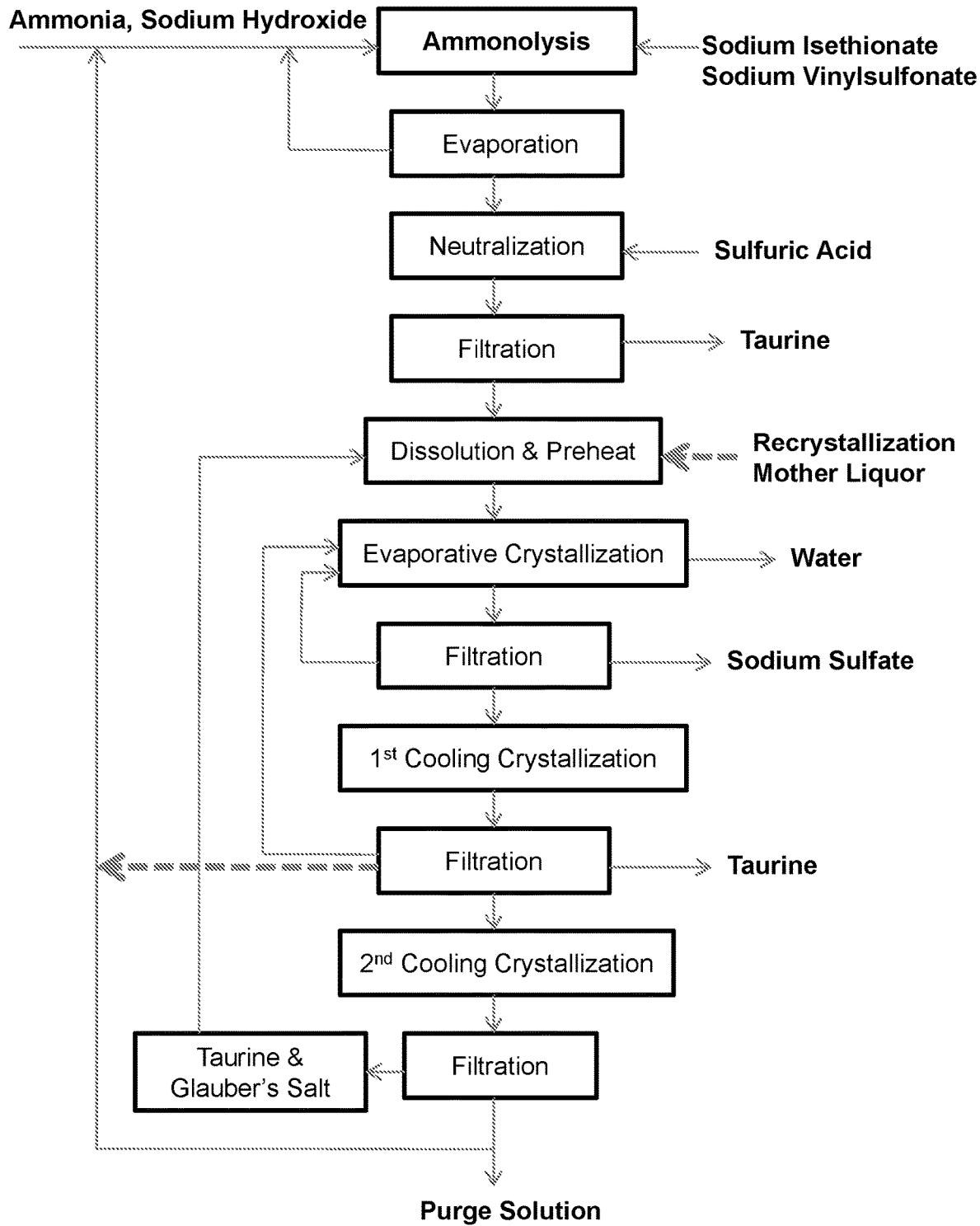
FIG. 1. Schematic flowchart for the cyclic production of taurine from sodium isethionate or sodium vinyl sulfate.

The present invention relates to a cyclic process for the production of taurine from alkali isethionate, which is a key intermediate for the ethylene oxide, ethanol, and ethylene processes. This cyclic process is also applied to the production of taurine from alkali vinyl sulfonate, another intermediate for the ethanol and ethylene processes.

For the production of taurine, sodium isethionate and sodium vinyl sulfonate are preferably used, but other alkali metals, i.e., lithium, potassium, and cesium, are equally suitable. In the drawings and following description, only sodium is used in replace of alkali metals to describe the process.

In order to achieve the cyclic process, the present invention discloses a novel finding and process for converting sodium ditaurinate and sodium tritaurinate, byproducts of the ammonolysis of sodium isethionate, to sodium taurinate under the ammonolysis conditions. According to the cyclic process in the present invention, sodium isethionate and sodium vinyl sulfonate are converted to sodium taurinate in a practically quantitative yield. A complete separation of taurine with sodium sulfate according to the process in the present invention ensures that taurine is obtained in high yield, i.e., greater than 90%, in particular greater than 95% on the basis of sodium isethionate or sodium vinyl sulfonate.

Although sodium ditaurinate and sodium tritaurinate are mentioned in the prior arts, preparation of pure products is not known. The present invention describes a method for the preparation of pure sodium ditaurinate and pure sodium tritaurinate from diethanolamine and triethanolamine, respectively.

To prepare sodium ditaurinate, diethanolamine is first reacted with excess thionyl chloride to form bis(2-chloroethyl)amine hydrochloride in quantitative yield, which undergoes sulfonation with sodium sulfite to yield the expected product. When triethanolamine is used in the same sequence of reactions, tris(2-chloroethyl)amine hydrochloride is obtained as an intermediate, disodium tritaurinate is obtained as an aqueous solution, along with sodium chloride. The reaction schemes are as follows:

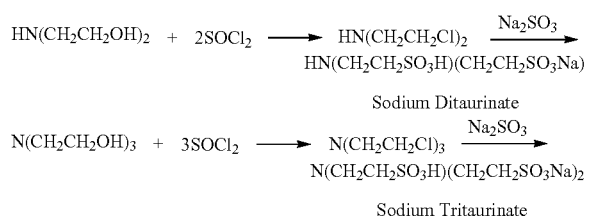

The sodium ditaurinate and sodium tritaurinate in the solution thus prepared are present in a neutral state. To the solution comprised of sodium ditaurinate or sodium tritaurinate is added sodium hydroxide to form disodium ditaurinate or trisodium tritaurinate. The molar amount of sodium hydroxide added is at least equal to the molar amount of sodium ditaurinate or sodium tritaurinate. The solution comprised of disodium ditaurinate or tri sodium tritaurinate is then added ammonia and is subjected to the ammonolysis reaction under the same conditions at a temperature of 220° C. for 2 hours, a mixture of similar compositions, i.e., sodium taurinate (74%), sodium ditaurinate (23%), and sodium tritaurinate (3%), is obtained. Clearly, an equilibrium state is reached among the three taurinates, irrespective of the starting materials.

This novel finding renders possible the cyclic process for preparing taurine from sodium isethionate and from sodium vinyl sulfonate, because the inevitable byproducts of the ammonolysis step, i.e., sodium ditaurinate and sodium tritaurinate, can be continuously converted to sodium taurinate in each successive cycle.

FIG. 1 describes the detailed unit operations for the cyclic process for the production and isolation of taurine from sodium isethionate. The cycle is equally applicable for the production of taurine from sodium vinyl sulfonate.

The cyclic process starts from the ammonolysis of sodium isethionate or sodium vinyl sulfonate in aqueous ammonia at a temperature of 150 to 270° C. under a pressure from the autogenous to 260 bars, and optionally, in the presence of catalysts. Usually, catalysts are the alkaline salts of sodium, potassium and lithium. Such salts are sodium hydroxide, potassium hydroxide, lithium hydroxide, sodium carbonate, potassium carbonate, lithium carbonate, sodium sulfate, sodium sulfite, potassium sulfate, potassium sulfite. Any one or a combination of two or more these salts can be used as catalyst to influence the reaction.

After the ammonolysis reaction, the excess ammonia is dispelled from the reaction solution and reclaimed for reuse. Sodium taurinate is obtained, along with sodium ditaurinate, sodium tritaurinate, and unreacted sodium isethionate.

The strongly basic solution is neutralized with sulfuric acid to pH 5-7 to yield mainly taurine, sodium sulfate, sodium ditaurinate, and sodium tritaurinate. The content of taurine and sodium sulfate is in a molar ratio of 1:0.5 to 1:0.6, and nearly the same in terms of their weight.

The initial solution is optionally concentrated, then cooled to 28 to 35° C., to crystallize taurine. The first batch of crude taurine is obtained by filtration, while sodium sulfate remains in solution. Lower temperature is to be avoided to prevent the crystallization of sodium sulfate.

Figure 2:
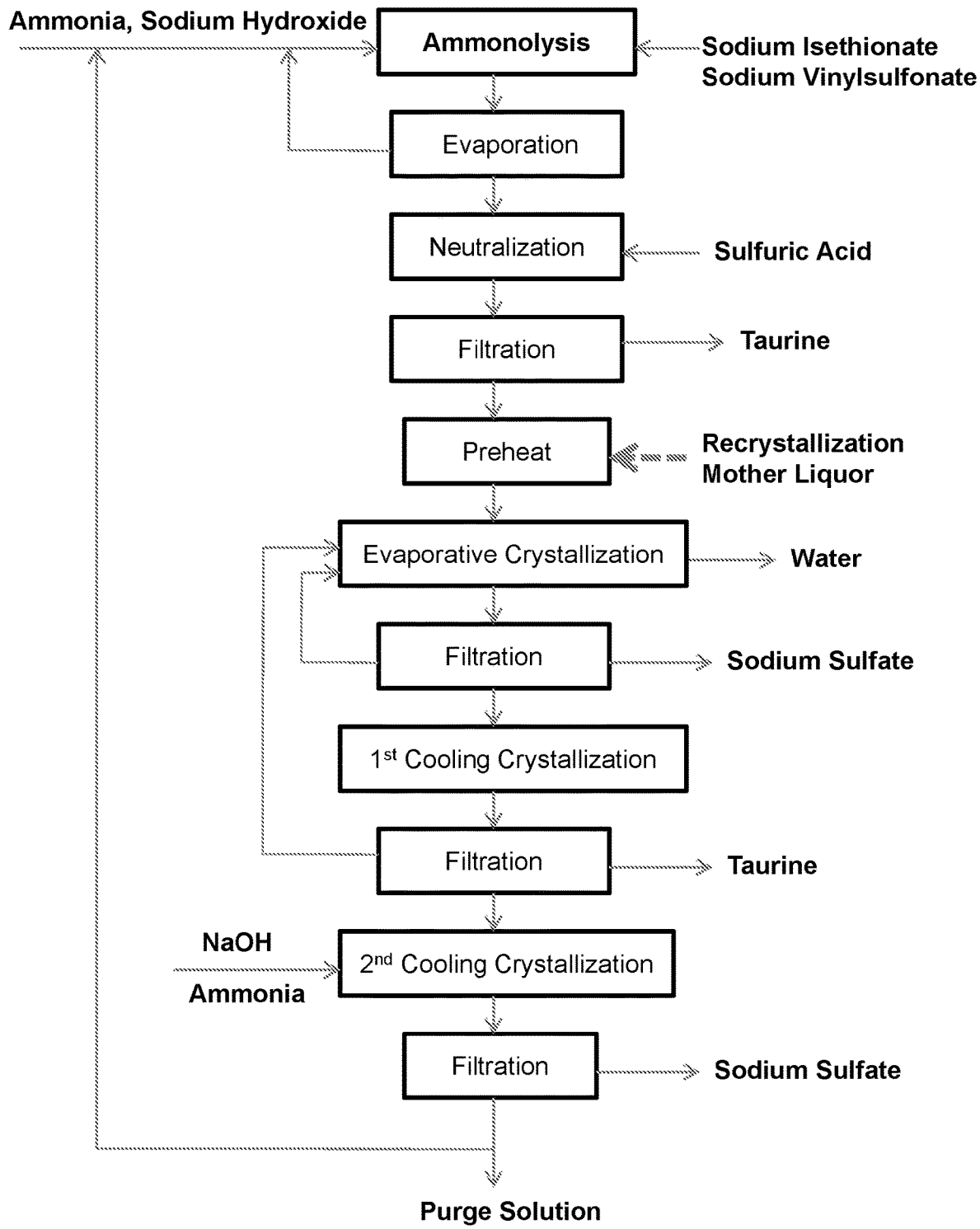
FIG. 2. Schematic flowchart for the cyclic production of taurine from sodium isethionate or sodium vinyl sulfate.

It is important to point out that sodium sulfate has the maximum solubility at a temperature of 33° C. as shown in FIG. 2. The solubility of sodium sulfate decreases slightly from 33 to 100° C., but drastically from 33 to 0° C. Moreover, sodium sulfate crystallizes as anhydrous form above 40° C., but as Glauber' s salt, i.e., sodium sulfate decahydrate at a temperature below 30° C.

The mother liquor is now consisted of about 30% of sodium sulfate and about 10% of taurine, along with various percentages of sodium ditaurinate and sodium tritaurinate. This solution is concentrated to about one half to one third of its original volume in an evaporative crystallizer, at a temperature from 70 to 95° C., preferably 75 to 85° C., to yield a suspension of sodium sulfate, which is removed by filtration at the same temperature. The temperature is kept high enough to prevent the crystallization of taurine at this stage.

The filtration mother liquor, now saturated with sodium sulfate and rich in taurine, is cooled to 33-35° C. in the $1^{st}$ cooling crystallizer to crystallize the second crop of crude taurine.

The cycle of evaporative crystallization at higher temperature, preferably from 75 to 85° C., to remove sodium sulfate, and the first cooling crystallization at lower temperature, preferably at 33-35° C., can be continued until the solid content of impurities, mainly sodium ditaurinate and sodium tritaurinate, accumulates to about 30% of the solid content in the mother liquor.

The mother liquor from the first cooling crystallization stage can be returned to the ammonolysis step. Preferably, the mother liquor is cooled to 10 to 15° C. in the $2^{nd}$ cooling crystallizer to co-crystallize taurine and sodium sulfate decahydrate, i.e., Glauber's salt. The co-crystalline mixture is removed from the mother liquor by centrifuge and returned to a dissolution and preheat unit for the evaporative crystallization step. It becomes apparent that lower temperature may be used, but excessive cooling is required to be economical. At higher temperature, removal of sodium sulfate is not complete.

The mother liquor from the second cooling crystallization stage is usually comprised of 25-30% of sodium ditaurinate and tritaurinate, 5-7% of taurine, and 7-8% of sodium sulfate. Sodium hydroxide is then added in an amount sufficient to turn taurine to sodium taurinate, sodium ditaurinate to disodium ditaurinate, and disodium tritaurinate to trisodium tritaurinate. In other words, the molar amount of sodium hydroxide is equal to, or slightly more than, the molar amount of total taurinates in the solution. After the addition of the at least equal molar amount of sodium hydroxide, the solution is comprised of disodium ditaurinate, trisodium tritaurinate, and sodium taurinate from the residual taurine. The solution is then saturated with ammonia to 15 to 28% and returned to the ammonolysis step for an ammonolysis resolution. Sodium taurinate is obtained in a yield of at least 70% from the total molar amount of sodium ditaurinate, sodium tritaurinate, and residual taurine in the mother liquor.

Optionally, the mother liquor solution comprised of disodium ditaurinate and trisodium tritaurinate may be combined with a new batch of sodium isethionate to obtain a solution comprised of sodium isethionate, di sodium ditaurinate, and tri sodium tritaurinate. This solution of sodium isethionate and the recycled mother liquor comprised of disodium ditaurinate and trisodium tritaurinate is returned to the ammonolysis stage for an ammonolysis reaction.

FIG. 2 illustrates another detailed unit operation for the cyclic process for the production and isolation of taurine from sodium isethionate, wherein sodium sulfate is separated from the mother liquor by adjusting the pH. The cycle is equally applicable to the production of taurine from sodium vinyl sulfonate.

Although the solubility of sodium sulfate and taurine shows the same decreasing trend as the temperature is lowered from 33° C. to 0° C., it has now been found that the solubility of taurine can be drastically increased by converting taurine to ammonium taurinate or sodium taurinate. This is achieved by adjusting the pH of the mother liquor from 5-6 to a pH of 10-12 by adding an aqueous solution of ammonia or sodium hydroxide, preferably sodium hydroxide. The solubility of sodium taurinate is found to be more than 90 g/100 g in water from 0° C. to 30° C. Taurine is soluble to 36 g in 100 g of 25% aqueous ammonia at room temperature. After the pH adjustment, the taurine is converted to sodium taurinate, sodium ditaurinate becomes di sodium ditaurinate, and sodium tritaurinate becomes trisodium tritaurinate in the mother liquor.

It is also found that the solubility of sodium sulfate can be further decreased by saturating aqueous solution of sodium sulfate with ammonia. It is thus possible to effectively separate sodium sulfate from residual taurine by simply adjusting the pH of the mother liquor and, optionally, saturating the mother liquor with ammonia. Upon cooling in the $2^{nd}$ cooling crystallizer, only sodium sulfate is precipitated from the mother liquor and removed by filtration.

If ammonia or ammonium hydroxide is used to adjust the pH, the mother liquor after removal of sodium sulfate needs to be fortified with sodium hydroxide to facilitate the ammonolysis of ditaurinate and tritaurinate to taurinate. The amount of sodium hydroxide used is from 2 to 30% of the amount of total taurinates. Preferably, the molar amount of sodium hydroxide is at least equal to the total molar amount of sodium ditaurinate, sodium tritaurinate, and residual taurine to form disodium ditaurinate, trisodium tritaurinate, and sodium taurinate.

The mother liquor from the $2^{nd}$ cooling crystallization stage after separating sodium sulfate is usually comprised of 25-30% of sodium ditaurinate and tritaurinate, 8-9% of sodium taurinate, and 5-8% of sodium sulfate. If sodium hydroxide is used to adjust the pH, this solution is then saturated with ammonia to 15 to 28% and returned to the ammonolysis step. If ammonium hydroxide is used to adjust the pH, then sufficient amount of sodium hydroxide is added to the solution. The solution is then saturated with ammonia to 15 to 28% and returned to the ammonolysis step for an ammonolysis resolution. Sodium taurinate is obtained in a yield of at least 70% from the total molar amount of sodium ditaurinate, sodium tritaurinate, and residual taurine in the mother liquor.

Optionally, the mother liquor solution comprised of disodium ditaurinate and trisodium tritaurinate may be combined with a new batch of sodium isethionate to obtain a solution comprised of sodium isethionate, disodium ditaurinate, and trisodium tritaurinate. This solution of sodium isethionate and the recycled mother liquor comprised of disodium ditaurinate and trisodium tritaurinate is returned to the ammonolysis stage for an ammonolysis reaction.

Some of the mother liquor from the $2^{nd}$ cooling crystallization needs to be purged from the cycle, when uncharacterized impurities start to adversely influence the quality of the product. The amount of purge solution in each cycle depends on the quality of starting materials, in particular, sodium isethionate and sodium vinyl sulfonate. If crude sodium isethionate in the ethylene oxide process is used, purge is required in about every five to eight cycles, because ethylene glycol, a byproduct from the reaction of ethylene oxide with water, starts to accumulate. If sodium isethionate is prepared from ethanol and ethylene, no purge is necessary at all.

Crude taurine obtained in the cyclic process is recrystallized from deionized water one or more times to yield a product of pharmaceutical grade. The recrystallization mother liquor may be reused several times until it affects the quality of the product obtained. This mother liquor, consisting of residual taurine, sodium sulfate, and impurities, is then sent to dissolution and preheat unit for the evaporative crystallization.

It should be appreciated that no waste is generated in the cyclic process according to the present invention for the production of taurine from ethanol and ethylene, because sodium sulfate, discharged in the cyclic process, is recycled continuously to prepare sodium isethionate and sodium vinyl sulfonate.

The process according to the present invention can be carried out discontinuously, semi-continuously, and continuously.

The present invention relates to a process for the production of taurine by the ammonolysis reaction of alkali isethionate in the presence of alkali ditaurinate or alkali tritaurinate, or their mixture, to inhibit the formation of byproducts, to increase the production yield, and to greatly reduce the waste discharge from the production process.

The process according to the present invention starts with mixing a solution of alkali ditaurinate or alkali tritaurinate, or their mixture, with alkali isethionate, followed by addition of an excess of ammonia. The ammonolysis is carried out at a temperature from 160° C. to 260° C. under the pressure from autogenous to 260 bars for 1 to 6 hours.

After the ammonolysis reaction, excess ammonia is dispelled from the reaction solution and reclaimed for reuse. A solution of alkali taurinate is obtained, along with alkali ditaurinate, alkali tritaurinate, and a trace amount of unreacted alkali isethionate.

The strongly basic solution is neutralized with an acid to pH 5-9 to yield a crystalline suspension of taurine in a solution of alkali salt, alkali ditaurinate, alkali tritaurinate, and a small amount of unreacted alkali isethionate. The initial suspension is optionally concentrated, then cooled to 28 to 35° C., to crystallize taurine. Taurine is obtained by means of solid-liquid separation.

The ratio of alkali ditaurinate, alkali tritaurinate, or their mixture, in relation to alkali isethionate can be varied from 0.01 to 10 by weight, preferably 0.1 to 1, more preferably 0.2-0.5, most preferably 0.3-0.4.

When the ratio is low, i.e., <0.1, a large amount of alkali isethionate is converted to alkali ditaurinate, instead of desired alkali taurinate, thus lowering the production yield and efficiency. When the ratio is too large, i.e., >1.0, the amount of the recycling byproducts becomes excessively large and the production capacity is lowered. Moreover, the cyclic process is not steady as the byproduct is indeed converted alkali taurinate.

Useful and effective catalysts are found among the alkali salts of hydroxide, carbonate, bicarbonate, hydrogen sulfate, sulfate, bisulfite, sulfite, nitrate, phosphate, chlorate, and perchlorate. Such salts are sodium hydroxide, lithium hydroxide, potassium hydroxide, lithium carbonate, lithium bicarbonate, sodium bicarbonate, sodium bicarbonate, potassium bicarbonate, lithium carbonate, sodium carbonate, potassium carbonate, lithium sulfate, sodium sulfate, potassium sulfate, lithium phosphate, sodium phosphate, potassium phosphate, lithium sulfite, sodium sulfite, and potassium sulfite.

The catalyst for the ammonolysis reaction of alkali isethionate can be one component or a combination of two or more components. Catalysts exogenous to the reaction system can be used, but catalysts inherently present in the production process are preferred. When sulfuric acid is used as a neutralizing acid, alkali salts of sulfate are preferred. Alkali salts of sulfite are preferred in the sulfur dioxide process.

Preferable catalysts are alkali hydroxide and the most preferable catalyst is sodium hydroxide.

The amount of the catalyst used is not limited, but is usually from 0.01 to 10 in molar ratio of the catalyst to alkali isethionate. The ratio is preferably in the range of 0.01 to 1, more preferably 0.1 to 0.5, most preferably 0.2 to 0.3. In the preferred range of the catalyst, the amount of alkali hydroxide is at least equal to the molar amount of alkali ditaurinate, alkali tritaurine, or their mixture in their respective mixture with alkali isethionate. A suitable amount of catalyst can be selected by those skilled in the art for the ammonolysis reaction to complete in desired time. After the addition of at least an equal molar amount of alkali hydroxide, the alkali ditaurinate and alkali tritaurinate in the mixture with alkali isethionate are converted to dialkali ditaurinate and trialkali tritaurinate, respectively.

The acid used in the neutralization process is selected from hydrochloric acid, hydrobromic acid, sulfuric acid, nitric acid, phosphoric acid, and organic carboxylic acids containing one to six carbons. Sulfuric acid is most preferably used.

Tables I to III demonstrate the effectiveness of the presence of alkali ditaurinate or alkali tritaurinate, or their mixture, on the ammonolysis of alkali isethionate to alkali taurinate, respectively. It becomes apparent that the conversion of alkali isethionate to alkali taurinate can reach nearly quantitative yield under disclosed conditions.

Table IV shows the effect of a different catalyst on the ammonolysis of alkali isethionate to alkali taurinate. When no catalyst is added to the ammonolysis reaction, low conversion of alkali isethionate is observed.

EXAMPLES

The following examples will illustrate the practice of this invention but are not intended to limit its scope.

Example 1

This example relates to the preparation of sodium ditaurinate and its reaction with aqueous ammonia under ammonolysis reaction conditions.

Into a 1 L flask, equipped a refluxing condenser, is added 31.5 g (0.30 mole) of diethanolamine and 300 mL of dichloroethane, then 51.0 mL of thionyl chloride. Solid suspension formed immediately after the addition of thionyl chloride and then dissolved upon warming to 50° C. During refluxing, the solid suspension is dissolved and then the crystalline solid appears. The crystalline suspension is refluxed while being stirred for 3 hrs. The reaction is quenched by adding 20 mL of methanol and the solvents are removed under vacuum. A white crystalline material, bis(2-chloroethyl)amine hydrochloride, weighted 53.0 g, is obtained in a quantitative yield.

To the flask is added 500 mL of deionized water, 100 g of sodium sulfite. The solution is stirred at a temperature first at 50-60° C. for 3 hrs, then at 95° C. for 4 hrs. HPLC and LC-MS shows complete conversion of the starting material to the desired sodium ditaurinate.

The excess sodium sulfite is destroyed by addition of 40 mL of 30% hydrochloric acid, followed by careful adjustment of pH to 6-7 with sodium carbonate. The solution consists of practically pure sodium ditaurinate and sodium chloride. The solution may be used directly in the ammonolysis reaction.

To obtain pure sodium ditaurinate, the aqueous solution is vacuum dried to give a white solid. Into the flask is added 600 mL of anhydrous methanol, and the suspension is refluxed for minutes to dissolve sodium ditaurinate in methanol. After filtration to remove sodium chloride, the methanol solution is cooled to room temperature to crystallize pure sodium ditaurinate, which is used as analytical standard.

Crude sodium ditaurinate, prepared from 0.30 mole of diethanolamine, is dissolved in 300 mL of water containing 26.0 g of sodium hydroxide. The solution is then mixed with 600 mL of 25% aqueous ammonia and heated in an autoclave at 220° C. for 2 hrs.

HPLC analysis of the reaction solution shows the formation of sodium taurinate (74%), sodium ditaurinate (24%), and sodium tritaurinate (2%) on the molar basis.

Example 2

This example relates to the preparation of sodium tritaurinate and its reaction with aqueous ammonia under ammonolysis reaction conditions.

Into a 1 L flask, equipped with a refluxing condenser, is added 29.8 g (0.20 mole) of triethanolamine, 300 mL of dichloroethane, then 51.0 mL of thionyl chloride. The mixture is heated to reflux for 4 hrs. The reaction is quenched by adding 20 mL of methanol. Removal of solvent gives a white crystalline mass of tris(2-chloroethylamine) hydrochloride in quantitative yield.

To the flask is added 500 mL of deionized water, 100 g of sodium sulfite. An oil phase is separated first. After heating at 60° C. for 2 hrs and 98° C. for 5 hrs, the oil phase disappears and a clear solution is obtained. HPLC and LC-MS shows complete conversion of the starting material to the desired sodium tritaurinate.

The crude reaction solution is transferred to a 2 L autoclave, to which 26 g of sodium hydroxide and 600 mL of 25% aqueous ammonia are added. The autoclave is heated to 220° C. for 2 hrs to carry out the ammonolysis reaction.

HPLC and LC-MS analysis shows that sodium tritaurinate is converted to a mixture of sodium taurinate (72%), sodium ditaurinate (23%), and sodium tritaurinate (5%) on the molar basis.

Example 3

This example demonstrates the conversion of sodium ditaurinate and sodium tritaurinate in the recrystallization mother liquor to sodium taurinate.

To 200 mL of the mother liquor from $2^{nd}$ cooling crystallization stage, composed of sodium ditaurinate (25% by wt), sodium tritaurinate (3% by wt), taurine (5% by wt), and sodium sulfate (6% by wt), is added 15 g of sodium hydroxide, 500 mL of 25% aqueous ammonia. The solution is heated in a 2 L autoclave at 220° C. for 2 hrs to carry out the ammonolysis reaction.

HPLC and LC-MS analysis shows that the reaction solution is comprised of the following taurinates: sodium taurinate (76%), sodium ditaurinate (21%), and sodium tritaurinate (3%) on the molar basis.

Example 4

This example is directed to a process for the separation of taurine from sodium sulfate and from sodium ditaurinate and sodium tritaurinate.

A starting solution is prepared by first boiling the solution from the ammonolysis reaction to remove excess ammonia, and then adding enough sulfuric acid to pH 5-7. The solution is consisted of 30% taurine, 26% sodium sulfate, and 7% sodium di- and tri-taurinates.

2000 g of the starting solution is cooled from 80° C. to 33° C. to form a slurry consisting essentially of the first crop of crystallized taurine, which is separated by filtration at 33° C. and washed with 100 g of cold water. The recovered taurine is dried and weighed 398 g.

The separated mother liquor, weighed 1580 g, is boiled to evaporate to 900 g to form a slurry of sodium sulfate. This slurry is cooled to 80° C. and filtered to recover sodium sulfate, weighed 304 g.

The mother liquor, containing 202 g of taurine and 216 g of sodium sulfate, is cooled to 33° C. to form a second slurry of taurine. After filtration and washing with cold water, 124 g of taurine is obtained.

The mother liquor from the previous step, now containing 78 of taurine and 216 g of sodium sulfate, is cooled to 10° C. in 2 hrs to obtain slurry of taurine and Glauber's salt. The crystalline solid is obtained as a mixture of taurine and sodium sulfate decahydrate.

This final mother liquor, about 500 g, is consisted of sodium ditaurinate and tritaurinate (28%, 140 g), taurine (24 g, 4.8%), and sodium sulfate (35 g, 7%). This solution is used for the ammonolysis reaction.

Example 5

This example is directed to a process for the separation of sodium sulfate from sodium taurinate, sodium ditaurinate, and sodium tritaurinate.

A starting solution is prepared by first boiling the solution from the ammonolysis reaction to remove excess ammonia, and then adding enough sulfuric acid to pH 5-7. The solution is consisted of 30% taurine, 26% sodium sulfate, and 7% sodium di- and tri-taurinates.

2000 g of the starting solution is cooled from 80° C. to 33° C. to form a slurry consisting essentially of the first crop of crystallized taurine, which is separated by filtration at 33° C. and washed with 100 g of cold water. The recovered taurine is dried and weighed 398 g.

The separated mother liquor, weighed 1580 g, is boiled to evaporate to 900 g to form a slurry of sodium sulfate. This slurry is cooled to 80° C. and filtered to recover sodium sulfate, weighed 304 g.

The mother liquor, containing 202 g of taurine and 216 g of sodium sulfate, is cooled to 33° C. to form second slurry of taurine. After filtration and washing with cold water, 124 g of taurine is obtained.

The mother liquor from the previous step, now containing 78 of taurine and 216 g of sodium sulfate, is added a solution of sodium hydroxide to pH 11, saturated with ammonia, and cooled to 10° C. in 2 hours to obtain a slurry of sodium sulfate, which is removed by filtration.

This final mother liquor, about 500 g, is consisted of sodium ditaurinate and tritaurinate (28%, 140 g), sodium taurinate (78 g, 15%), and sodium sulfate (35 g, 7%). This solution is used for the ammonolysis reaction.

Example 6

This set of examples relates to the ammonolysis of sodium isethionate in the presence of sodium ditaurinate and in the presence of sodium hydroxide.

All examples are for 0.05 mole of sodium isethionate, dissolved in 35 mL of 20% aqueous ammonia solution in a molar ratio of 1:8 for sodium isethionate to ammonia. Calculated amount of sodium ditaurinate and sodium hydroxide is then added to the solution. The ammonolysis reaction is carried out in an 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[Sodium Isethionate]
Di+Tritaurinate Yield (%)=[Di+Tritaurine-
Added Ditaurine]/[Sodium Isethionate]

TABLE I

Ammonolysis of Sodium Isethionate in the Presence of Sodium Ditaurinate

| Ex | Ditaurinate/ Isethionate (ratio by weight) | NaOH/ Isethionate (ratio by weight) | Taurinate (molar yield %) | Di+Tritaurinate (molar yield %) |
|---|---|---|---|---|
| 1 | 0 | 0.01 | 75 | 24 |
| 2 | 0.1 | 0.01 | 84 | 15 |
| 3 | 0.2 | 0.01 | 86 | 14 |
| 4 | 0.3 | 0.01 | 87 | 13 |
| 5 | 0.3 | 0.02 | 91 | 9 |
| 6 | 0.3 | 0.03 | 93 | 7 |
| 7 | 0.3 | 0.04 | 95 | 5 |
| 8 | 0.3 | 0.05 | 98 | 2 |
| 9 | 0.5 | 0.15 | 112 | −12 |
| 10 | 1.0 | 0.20 | 145 | −45 |

Example 7

This set of examples relates to the ammonolysis of sodium isethionate in the presence of sodium tritaurinate and in the presence of sodium hydroxide.

All examples are for 0.05 mole of sodium isethionate, dissolved in 35 mL of 20% aqueous ammonia solution in a molar ratio of 1:8 for sodium isethionate to ammonia. Calculated amount of sodium tritaurinate and sodium hydroxide is then added to the solution. The ammonolysis reaction is carried out in an 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[Sodium Isethionate]
Di+Tritaurinate Yield (%)=[Di+Tritaurine-
Added Tritaurine]/[Sodium Isethionate]

TABLE II

Ammonolysis of Sodium Isethionate in the Presence of Sodium Tritaurinate

| Ex | Tritaurinate/ Isethionate (ratio by weight) | NaOH/ Isethionate (ratio by weight) | Taurinate (molar yield %) | Di+Tritaurinate (molar yield %) |
|---|---|---|---|---|
| 11 | 0 | 0.01 | 76 | 24 |
| 12 | 0.1 | 0.01 | 83 | 16 |
| 13 | 0.2 | 0.01 | 86 | 14 |
| 14 | 0.3 | 0.01 | 87 | 13 |
| 15 | 0.3 | 0.02 | 88 | 11 |
| 16 | 0.3 | 0.03 | 94 | 6 |
| 17 | 0.3 | 0.04 | 94 | 5 |
| 18 | 0.3 | 0.05 | 98 | 2 |
| 19 | 0.5 | 0.15 | 121 | −20 |
| 20 | 1.0 | 0.20 | 151 | −49 |

Example 8

This set of examples relates to the ammonolysis of sodium isethionate in the presence of a mixture of sodium ditaurinate and sodium tritaurinate obtained from the mother liquor of taurine crystallization and in the presence of sodium hydroxide and sodium sulfate.

All examples are for 0.05 mole of sodium isethionate, dissolved in 35 mL of 20% aqueous ammonia solution in a molar ratio of 1:8 for sodium isethionate to ammonia. Calculated amount sodium hydroxide is then added to the solution. A mixture of sodium ditaurinate and sodium tritaurinate, obtained from the crystallization mother liquor described as in appl. Ser. No 14/120,046 is used. The ammonolysis reaction is carried out in a 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[ Sodium Isethionate]
Di+Tritaurinate Yield (%)=[Di+Tritaurine-
(Added Di+Tritaurine)]/[Sodium Isethionate]

TABLE III

Ammonolysis of Sodium Isethionate in the Presence of a Mixture of Sodium Ditaurinate and Sodium Tritaurinate

| Ex | (Di+Tritaurinate)/ Isethionate (ratio by weight) | NaOH/ Isethionate (ratio by weight) | Taurinate (molar yield %) | Di+Tritaurinate (molar yield %) |
|---|---|---|---|---|
| 21 | 0 | 0.01 | 81 | 19 |
| 22 | 0.1 | 0.01 | 84 | 16 |
| 23 | 0.2 | 0.01 | 87 | 12 |
| 24 | 0.3 | 0.01 | 87 | 13 |
| 25 | 0.3 | 0.02 | 88 | 11 |
| 26 | 0.3 | 0.03 | 95 | 4 |
| 27 | 0.3 | 0.04 | 96 | 4 |
| 28 | 0.3 | 0.05 | 98 | 2 |
| 29 | 0.5 | 0.15 | 126 | −26 |
| 30 | 1.0 | 0.20 | 154 | −53 |

Example 9

This set of examples shows the effect of a different catalyst on the ammonolysis of sodium isethionate in the presence of a mixture of sodium ditaurinate and sodium tritaurinate obtained from the mother liquor of taurine crystallization.

All examples are for 0.05 mole of sodium isethionate, dissolved in 35 mL of 20% aqueous ammonia solution in a molar ratio of 1:8 for sodium isethionate to ammonia. Calculated amount catalyst and a mixture of sodium ditaurinate and sodium tritaurinate, obtained from the crystallization mother liquor described as in appl. Ser. No 14/120, 046, are added to the solution. The ratio of (di+tritaurinate)/ isethionate by weight is fixed at 0.3. The ammonolysis reaction is carried out in an 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[ Sodium Isethionate]
Di+Tritaurinate Yield (%)=[Di+Tritaurine-
(Added Di+Tritaurine)]/[ Sodium Isethionate]

TABLE IV

Effect of Catalyst on Ammonolysis of Sodium Isethionate in the Presence of a Mixture of Sodium Ditaurinate and Sodium Tritaurinate

| Ex | Catalyst | Catalyst/ Isethionate (ratio by weight) | Taurinate (molar yield %) | Di+Tritaurinate (molar yield %) |
|---|---|---|---|---|
| 31 | None | 0 | 55 | 12 |
| 32 | Sodium carbonate | 0.15 | 96 | 4 |
| 33 | Sodium sulfite | 0.15 | 95 | 4 |
| 34 | Potassium hydroxide | 0.10 | 97 | 3 |
| 35 | Potassium carbonate | 0.15 | 94 | 6 |
| 36 | Potassium sulfite | 0.10 | 94 | 6 |
| 37 | Lithium hydroxide | 0.03 | 95 | 4 |
| 38 | Lithium carbonate | 0.10 | 93 | 7 |
| 39 | Sodium phosphate | 0.15 | 97 | 3 |
| 40 | Potassium phosphate | 0.15 | 96 | 4 |
| 41 | Potassium acetate | 0.20 | 96 | 4 |
| 42 | Sodium acetate | 0.20 | 96 | 4 |

It will be understood that the foregoing examples and explanation are for illustrative purposes only and that various modifications of the present invention will be self-evident to those skilled in the art. Such modifications are to be included within the spirit and purview of this application and the scope of the appended claims.

What is claimed is:

1. A process for producing taurine in a molar yield of at least 80% on the basis of alkali isethionate in more than one vessel, comprising:
    (a) adding alkali hydroxide and excess ammonia to a solution comprised of alkali isethionate and alkali ditaurinate; wherein the molar amount of alkali hydroxide is at least equal to the molar amount of total taurinates comprising alkali ditaurinate in the solution; and wherein the alkali is lithium, sodium, potassium, or a mixture thereof;
    (b) subjecting the solution of step (a) to an ammonolysis;
    (c) removing excess ammonia from the solution of step (b) to obtain a solution comprising alkali taurinate; and
    (d) converting the alkali taurinate of step (c) to taurine.

2. The process according to claim 1, wherein the solution comprised of alkali isethionate and alkali ditaurinate is comprised of the mother liquor solution produced from alkali isethionate in a process comprising the steps of:
    (1) adding excess ammonia to a solution comprised of alkali isethionate; wherein the alkali is lithium, sodium, potassium, or a mixture thereof;
    (2) subjecting the solution of step (1) to an ammonolysis;
    (3) removing excess ammonia from the solution of step (2) to obtain a solution comprising alkali taurinate;
    (4) converting the alkali taurinate of step (3) to taurine; and
    (5) isolating the taurine of step (4) to form a mother liquor solution.

3. The process according to claim 2, wherein the mother liquor solution is comprised of alkali ditaurinate, alkali isethionate, and alkali tritaurinate.

4. The process according to claim 2, wherein the mother liquor solution is comprised of alkali isethionate and alkali ditaurinate.

5. The process according to claim 1, wherein the alkali taurinate is converted to taurine by reacting with an acid.

6. The process according to claim 5, wherein the acid is selected from the group consisting of sulfuric acid, hydrochloric acid, hydrobromic acid, nitric acid, phosphoric acid, and organic carboxylic acid.

7. The process according to claim 1, wherein the alkali taurinate is converted to taurine by reacting with an ion exchange resin.

8. The process according to claim 1, wherein the alkali hydroxide is added to the solution comprised of alkali isethionate and alkali ditaurinate to a pH of at least 10.

9. The process according to claim 1, wherein the excess ammonia is recovered for reuse.

10. The process according to claim 1, wherein the alkali hydroxide is added to the solution comprised of alkali isethionate and alkali ditaurinate to a pH of at least 9.

11. The process according to claim 2, wherein the mother liquor solution is comprised of alkali ditaurinate.

12. The process according to claim 2, wherein the mother liquor solution is comprised of alkali tritaurinate.

13. The process according to claim 2, wherein the mother liquor solution is comprised of unreacted alkali isethionate.

14. The process according to claim 1, wherein the solution comprised of alkali isethionate and alkali ditaurinate is the mother liquor solution produced from alkali isethionate in a process comprising the steps of:
    (1) adding excess ammonia to a solution comprised of alkali isethionate; wherein the alkali is lithium, sodium, potassium, or a mixture thereof;
    (2) subjecting the solution of step (1) to an ammonolysis;
    (3) removing excess ammonia from the solution of step (2) to obtain a solution comprising alkali taurinate;
    (4) converting the alkali taurinate of step (3) to taurine; and
    (5) isolating the taurine of step (4) to form a mother liquor solution.

15. The process according to claim 14, wherein the mother liquor solution is comprised of unreacted alkali isethionate.

16. The process according to claim 14, wherein the mother liquor solution is comprised of alkali ditaurinate.

17. The process according to claim 14, wherein the mother liquor solution is comprised of alkali isethionate and alkali ditaurinate.

18. The process according to claim 14, wherein the mother liquor solution is comprised of alkali tritaurinate.

19. The process according to claim 1, wherein the taurinates are selected from the group consisting of taurine, sodium ditaurinate, sodium tritaurinate, and a mixture thereof.

* * * * *